(12) United States Patent
Leithe et al.

(10) Patent No.: US 6,435,187 B1
(45) Date of Patent: Aug. 20, 2002

(54) BANDAGE FOR RELIEF AND MASSAGE

(76) Inventors: Kristen Leithe; Vigdis Marie Leithe, both of N-6530, Bruhagen (NO)

( * ) Notice: Subject to any disclaimer, the term of this patent is extended or adjusted under 35 U.S.C. 154(b) by 0 days.

(21) Appl. No.: 08/913,158

(22) PCT Filed: Feb. 7, 1996

(86) PCT No.: PCT/NO96/00028
§ 371 (c)(1),
(2), (4) Date: Dec. 9, 1997

(87) PCT Pub. No.: WO96/25900
PCT Pub. Date: Aug. 29, 1996

(30) Foreign Application Priority Data

Feb. 21, 1995 (NO) .................................................. 950641

(51) Int. Cl.⁷ ............................................... A61B 19/00
(52) U.S. Cl. ...................... 128/869; 128/878; 128/879; 128/882
(58) Field of Search ................................ 128/846, 869, 128/870, 878, 879, 882; 602/6, 9, 13, 23, 28, 62, 63

(56) References Cited

U.S. PATENT DOCUMENTS

| | | | | |
|---|---|---|---|---|
| 4,128,097 A | * | 12/1978 | Bilinsky | 602/63 |
| 4,657,003 A | * | 4/1987 | Wirtz | 602/13 |
| 4,854,314 A | * | 8/1989 | Martin | 128/205.27 |
| 4,885,811 A | * | 12/1989 | Hayes | 128/870 |
| 5,662,991 A | * | 9/1997 | Smolik | 442/319 |

* cited by examiner

Primary Examiner—Michael A. Brown
(74) Attorney, Agent, or Firm—James E. Walton; Hill & Hunn, LLP

(57) ABSTRACT

Massage and relief bandage device for persons vulnerable to bedsores (decuibitus ulcer), having a bag device of a flexible material, particularly cloth, which is filled with foamed plastic beads. The cloth material is a porous material, permeable to air, and the bag device has a plurality of chambers divided by non-filled parts that extend to the edges of the bandage device. The amount of filling material in the chambers is low to allow displacement of the granular material without particular outside pressure.

6 Claims, 3 Drawing Sheets

BANDAGE FOR RELIEF AND MASSAGE

Figure 1:
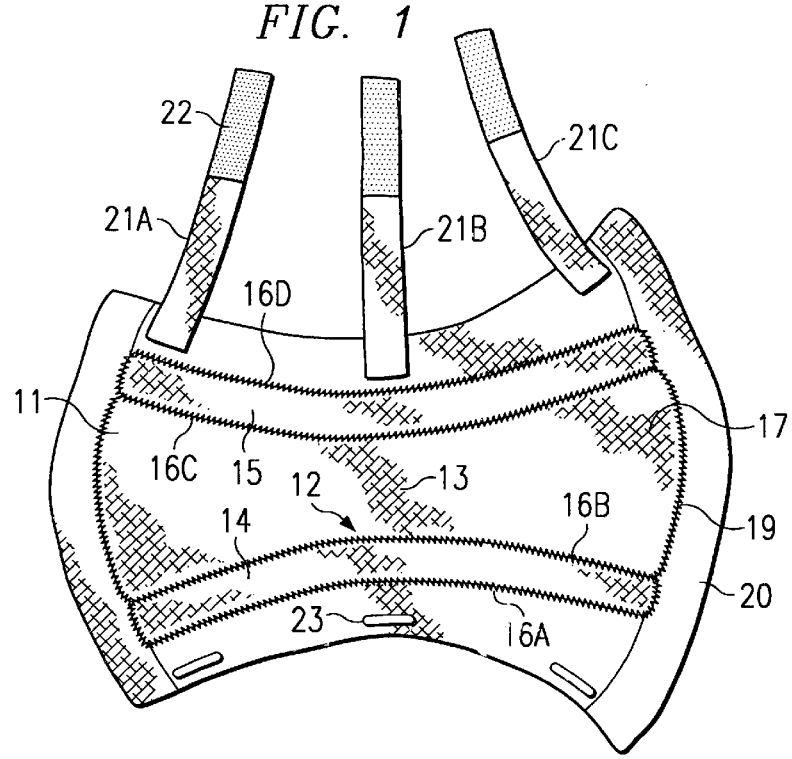

The invention relates to a massage and relief bandage device as stated in the introductory part of claim 1, for persons vulnerable to bedsores (decubitus ulcer), particularly patients in nursing homes, hospitals and in home care (terminal care).

BACKGROUND

Persons who are being immobilized in a bed or a wheelchair chair for long periods of time are vunerable to bedsores (decubitus ulcer) and similar sores due to unilateral and enduring pressure of limbs. Most vulnerable are the lumbar regions, the hips, the ankles, and the elbows, i.e. the parts of the body most exposed to pressure.

It has been proposed to use thick fibre mats, foam plastic, and other pressure distributing materials. A common disadvantage with such measures is enveloping the vulnerable area thus resulting in a temperature increase with the risk of sweat and moisture.

It is known to use small plastic spheres in cushions to avoid bedsores. It is known e.g. from U.S. Pat. No. 4,425,676 (Crane) to manufacture a cushion with several parallel chambers and with light plastic beads of preferably the same size and with a diameter from 0.5 to 3 mm. Additionally, this cushion is provided with a blower to create an air flow and keep the beads in motion. This solution is however expensive and creates significant hygene problems.

In U.S. Pat. No. 4,657,003 (Wirtz) it is proposed to provide an immobilizing device to keep a joint, e.g. an elbow, restrained. In a bag, beads of preferably the same size and a diameter of over 5 mm, are provided. When the known bandaging bag is arranged and the joint is in its desired position, the air is evacuated to compact and lock the beads in position.

From German Offenlegungsschrift 2,408,726 (Dyson) it is known to use a combination of small beads and a fluidmedium to prevent bedsores.

From German Offenlegungsschrift 4,219,698 it is known to actively exert a pressure by using beads in a cover. In this case the purpose is to provide an active massage as part of therapeutical treatment.

Common to the prior art solutions of the bedsore problem, is the deficiency in addressing the most important issues, i.e. stimulating blood circulation and provision of air to the body and corresponding transfer of heat and sweat. The hygenic conditions have also been unsatisfactory.

OBJECTS

The main object of the invention is to provide a massage and relief bandage device which solves the problem of reducing pressure and demoisturing the skin. It should also stimulate blood circulation, to reduce the tendency for wounds to develop which is inherent in reduced blood circulation.

A particular object is to provide a massage and relief bandage device which permits access of air to that part of the body covered by the device. It should also be easy to clean.

A more particular object is to provide a massage and relief bandage device, which may be manufactured so as to be disposable.

THE INVENTION

The main advantage of this design is the contribution to stimulation of blood circulation in the areas of contact, without preventing access of air to the part of the body covered by the device.

Further features of the invention are stated in claims 2–8.

EXAMPLE

Figure 2:
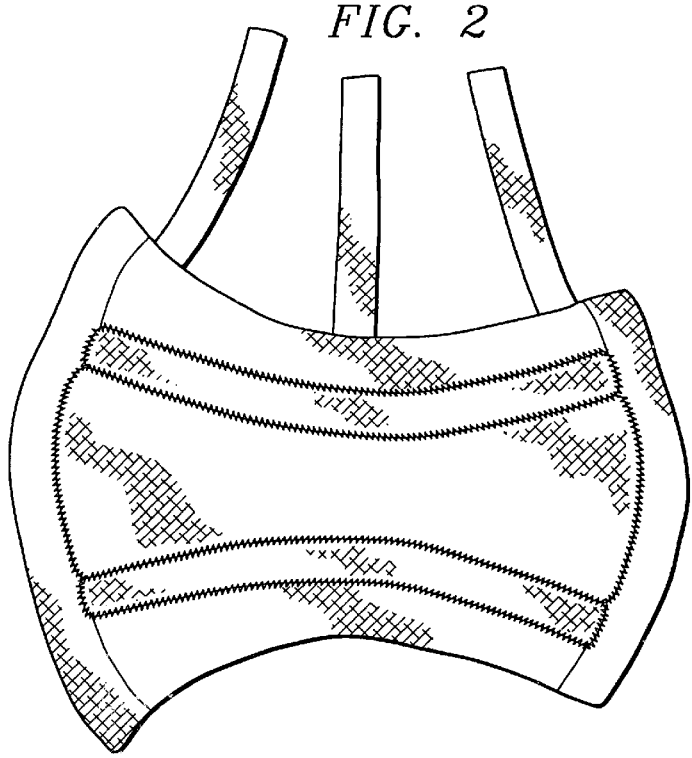
Figure 3:
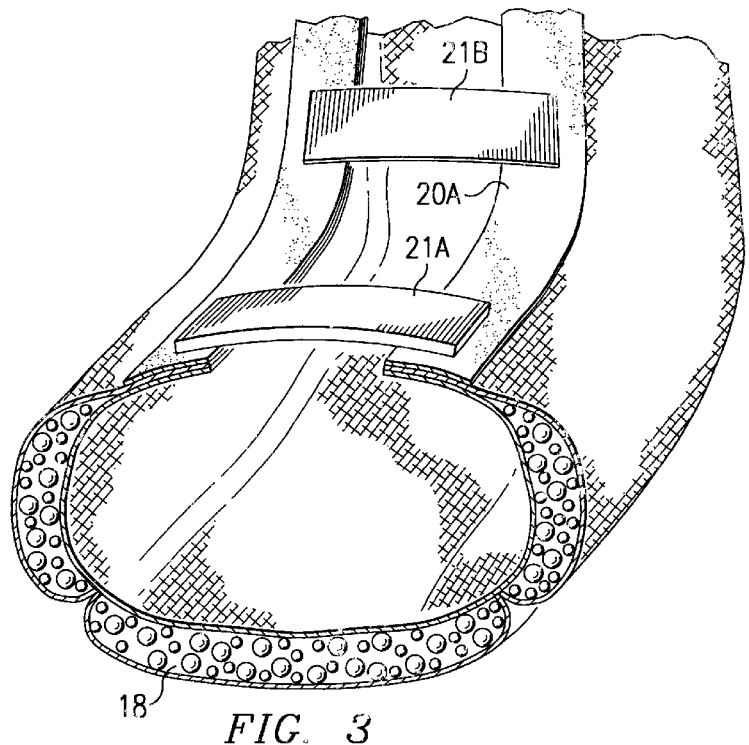
Figure 4:
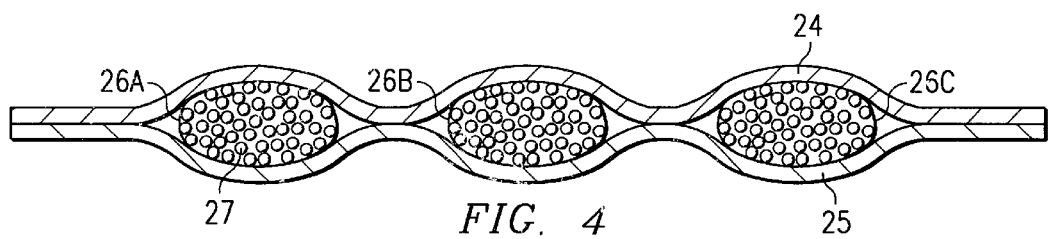
Figure 5:
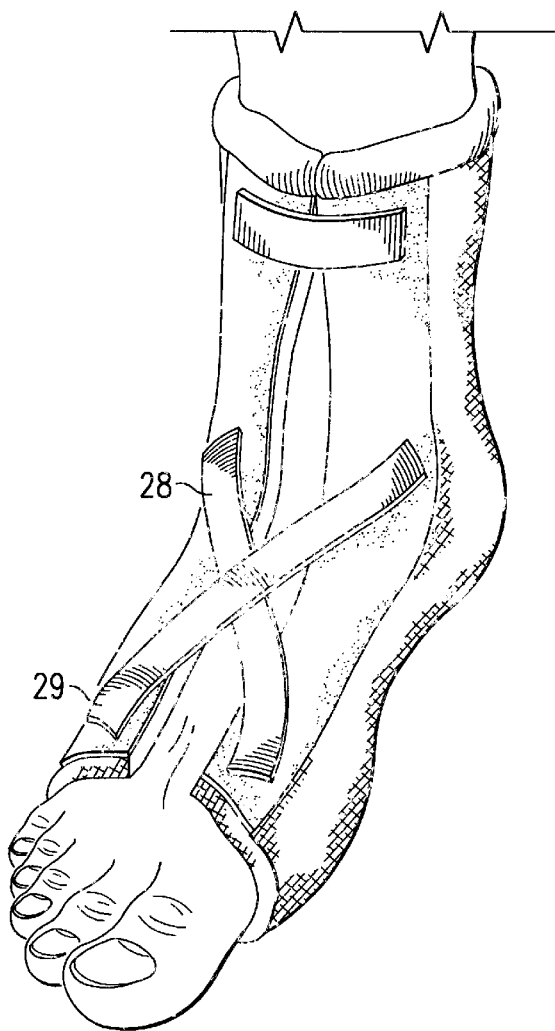
Figure 6:
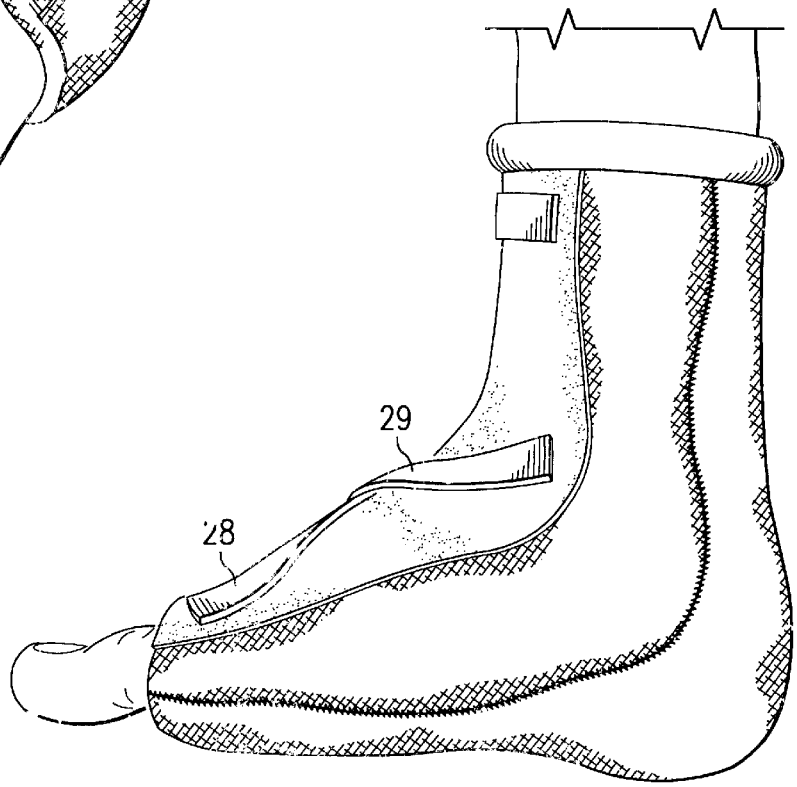

The invention is described more completely with reference to the embodiments illustrated in the drawings, in which FIG. 1 is a front view of a massage and relief bandage device according to the invention, FIG. 2 is a back view of the device shown in FIG. 1, FIG. 3 is a cross section through the device of FIG. 1 and 2 when in use, FIG. 4 is a cross section through a disposable bandage device according to the invention, and FIGS. 5 and 6 are a perspective view and a side view respectively of an alternative embodiment.

In FIGS. 1 and 2 there is shown a massage and relief bandage device for use on an elbow or a heel of a foot. It has at bag body comprising a central longitudinal chamber 11 with a transverse restriction 12 in the middle 13, and an adjoining chamber 14 and 15 of constant width on each side. The three chambers 11, 14, 15 are created with longitudinal seams 16A–D on a double web 17. It is particularly advantageous to use organic material, such as cotton material or linen. Organic material will have a higher absorption capacity. The density may be approximately 110 grams per square meter, preferably not exceeding 150 grams per square meter.

Stuffing with a granular material 18 (FIG. 3) may be carried out before sewing a final cross seam 19, as a closure. The cloth is sized to have an unstuffed edge 20 along all edges. The purpose of the edge 20 is to stabilize the bandage device, when attached to a user.

To attach the bandage device to the foot or arm of a user, the device of the example is provided with three straps 21A–C extending from one of the longitudinal edges. The ends of straps 21A–C are provided with velcro-fasteners 22, the straps being arranged to be hooked into corresponding loops 23 at the opposite edge, to be folded back for attachment.

In FIG. 3 an alternative embodiment is shown, in which one of the edges 20 is provided with an attachment ribbon 20A for the velcro fasteners on the straps 21A–B. The stuffing 18 may be expanded polystyrene.

In FIG. 4 there is shown a section through a disposable device formed by laminating two layers 24 and 25 of non-woven material, e.g. paper plies, enclosing three net bags 26A–C which are stuffed with hollow plastic beads 27. The net bags 26A–C are manufactured of a net tube with a mesh size which restrains the beads 27. After stuffing the tubular net bag, it is divided in suitable sections which are closed at the ends by prior art techniques. The net bags 26A–C take the pressure of the beads and allow the use of a light and open cover material. Therefore a simple and inexpensive bandage device, is provided which may be disposed after use like a disposable diaper. To maintain the disposable bandage device on the user, e.g. on an arm or a foot, an elastic net collar or muff can be drawn on the bandage device. Alternatively, adhesive tapes can be used. The layers of non-woven material 24 and 25 can be connected by dots of adhesive.

In FIGS. 5 and 6 there is shown a bandage device correspond to the bandage device of FIG. 3, with the exception that straps 28 and 29 are being crossed over. The purpose is to maintain a foot disposed at a right angle. This is needed by patients after suffering paralysis, e.g. by cerebral haermorrhage, to avoid a permanent deformation of the foot, called "drop foot".

What is claimed is:

1. Massage and relief bandage device for persons vulnerable to bedsores (decubitus ulcers), comprising:
   a bag device of a flexible material, particularly cloth, which is filled with a granular material, particularly foamed plastic beads;
   wherein the cloth material is a porous material, permeable to air;
   wherein the bag device has a plurality of chambers divided by non-filled parts;
   wherein the non-filled parts extend to the edges of the bandage device;
   wherein the chambers are not completely filled, so as to permit displacement of the granular material without particular outside pressure;
   wherein the filling material is beads with closed surfaces; and
   wherein the cloth is a textile with a density under 150 grams per square meter, preferably about 110 grams per square meter, preferably an organic material.

2. Massage and relief bandage device for persons vulnerable to bedsores (decubitus ulcers), comprising:
   a bag device of a flexible material, particularly cloth, which is filled with a granular material, particularly foamed plastic beads;
   wherein the cloth material is a porous material, permeable to air;
   wherein the bag device has a plurality of chambers divided by non-filled parts;
   wherein the non-filled parts extend to the edges of the bandage device;
   wherein the chambers are not completely filled, so as to permit displacement of the granular material without particular outside pressure;
   wherein the filling material is beads with closed surfaces;
   the cloth material is of porous paper or plies; and
   the device being provided to be maintained on the user by an elastic net tube.

3. A massage and relief bandage device for persons vulnerable to bedsores (decubitus ulcers), comprising:
   a flexible, air-permeable bag portion adapted to receive a granular material;
   the bag portion having a plurality of chambers separated by partitions;
   the partitions extending to the edges of the bandage device;
   at least one longitudinal, centrally located chamber;
   a transverse partition for restricting the centrally located chamber; and
   the chambers being only partially filled with the granular material, so as to allow displacement of the granular material without outside pressure;
   wherein the bag portion is made from a porous cloth material; and
   wherein the cloth material is an organic textile with a density under 150 grams per square meter.

4. A massage and relief bandage device for persons vulnerable to bedsores (decubitus ulcers), comprising:
   a top layer of non-woven material;
   a bottom layer of non-woven material coupled to the top layer of non-woven material;
   a plurality of flexible, air-permeable net bag members disposed between the top layer and bottom layer of non-woven material;
   the net bag members being partitioned into chambers, the chambers being adapted to receive and retain a granular material; and
   an elastic member for drawing over the device to maintain the device on a user.

5. A massage and relief bandage device for persons vulnerable to bedsores (decubitus ulcers), comprising:
   a flexible, air-permeable bag portion adapted to receive a granular material;
   the bag portion having a plurality of chambers separated by partitions;
   the partitions extending to the edges of the bandage device;
   at least one longitudinal, centrally located chamber;
   a transverse partition for restricting the centrally located chamber; and
   the chambers being only partially filled with the granular material, so as to allow displacement of the granular material without outside pressure;
   wherein the bag portion is made from a porous cloth material; and
   wherein the cloth material is an organic textile with a density under 150 grams per square meter.

6. A massage and relief bandage device for persons vulnerable to bedsores (decubitus ulcers), comprising:
   a flexible, air-permeable bag portion adapted to receive granular material;
   the bag portion having a plurality of chambers separated by partitions;
   the partitions extending to the edges of the bandage device;
   an elastic net member carried by the bag portion for maintaining the massage and relief bandage on a user; and
   the chambers being only partially filled with the granular material, so as to allow displacement of the granular material without outside pressure.

* * * * *